United States Patent
Lee et al.

(10) Patent No.: US 9,476,083 B2
(45) Date of Patent: Oct. 25, 2016

(54) TIME-TEMPERATURE INDICATOR, METHOD FOR MANUFACTURING THE TIME-TEMPERATURE INDICATOR, QUALITY GUARANTEE SYSTEM USING THE TIME-TEMPERATURE INDICATOR, AND QUALITY GUARANTEE METHOD USING THE QUALITY GUARANTEE SYSTEM

(75) Inventors: Seung Ju Lee, Seoul (KR); Seung Won Jung, Gyeonggi-do (KR)

(73) Assignee: Dongguk University Industry-Academic Cooperation Foundation, Seoul (KR)

( * ) Notice: Subject to any disclaimer, the term of this patent is extended or adjusted under 35 U.S.C. 154(b) by 124 days.

(21) Appl. No.: 14/127,311

(22) PCT Filed: Jun. 27, 2012

(86) PCT No.: PCT/KR2012/005083
§ 371 (c)(1),
(2), (4) Date: Dec. 18, 2013

(87) PCT Pub. No.: WO2013/002552
PCT Pub. Date: Jan. 3, 2013

(65) Prior Publication Data
US 2014/0127738 A1    May 8, 2014

(30) Foreign Application Priority Data

Jun. 28, 2011 (KR) .................. 10-2011-0063075

(51) Int. Cl.
*C12Q 1/02* (2006.01)
*G01N 31/22* (2006.01)
*G01N 21/47* (2006.01)

(52) U.S. Cl.
CPC .................. *C12Q 1/02* (2013.01); *G01N 21/47* (2013.01); *G01N 31/229* (2013.01)

(58) Field of Classification Search
None
See application file for complete search history.

(56) References Cited

U.S. PATENT DOCUMENTS 6,270,724 B1    8/2001  Woodaman
7,157,048 B2    1/2007  Goldsmith et al.
(Continued)

FOREIGN PATENT DOCUMENTS

JP         2007525664 A       9/2007
WO    WO-2007116071 A1    10/2007

OTHER PUBLICATIONS

JP-2007-525664; 2007; English translation, performed Jul. 16, 2015.*

(Continued)

*Primary Examiner* — Karen Cochrane Carlson
*Assistant Examiner* — Jennifer M. H. Tichy
(74) *Attorney, Agent, or Firm* — Lewis Roca Rothgerber Christie LLP (57) ABSTRACT

The present invention relates to a two-dimensional code-type time-temperature indicator the color or shape of which changes in accordance with time and temperature conditions, and to a method for manufacturing the time-temperature indicator, to a quality guarantee system using the time-temperature indicator, and to a quality guarantee method using the quality guarantee system. The time-temperature indicator comprises: nanobeads containing a microorganism for generating lactic acids using nutrient components, an indicating agent for indicating the change in color by means of the generated lactic acids, an immobilization material for immobilizing the microorganism, the indicating agent, and the nutrient components; a base having a bonding layer; and a cover film.

10 Claims, 8 Drawing Sheets (56) References Cited

U.S. PATENT DOCUMENTS

2007/0275467 A1 11/2007 Louvet et al.
2009/0122829 A1* 5/2009 Perez-Luna .............. G01K 3/04
374/102

OTHER PUBLICATIONS

International Search Report and Written Opinion for PCT/KR2012/005083 mailed Dec. 14, 2012 (8 pages).

Choi, Dong Yeol, et al.: "Fabrication and Characteristics of Microbial Time Temperature Indicators from Bio-Paste Using Screen Printing Method," Jul. 15, 2013 (31 pages).

Vaikousi, H., et al.: "Development of Microbial Time/Temperature Indicator Prototype for Monitoring the Microbiological Quality of Chilled Foods," Applied and Environmental Microbiology, May 2008, vol. 74, No. 10, pp. 3242-3250.

"Response of Microbial Time Temperature Indicator to Quality Indices of Chicken Breast Meat During Storage," Food Science and Biotechnology, Korean Society of Food Science and Technology, ISSN 1226-7708 (print), ISSN 2092-6459 (online), 2013 (34 pages).

* cited by examiner

REMAINING
EXPIRATION DATE
12 MONTH

REMAINING
EXPIRATION DATE
9 MONTH

REMAINING
EXPIRATION DATE
6 MONTH

REMAINING
EXPIRATION DATE
3 MONTH

TIME-TEMPERATURE INDICATOR, METHOD FOR MANUFACTURING THE TIME-TEMPERATURE INDICATOR, QUALITY GUARANTEE SYSTEM USING THE TIME-TEMPERATURE INDICATOR, AND QUALITY GUARANTEE METHOD USING THE QUALITY GUARANTEE SYSTEM

CROSS REFERENCE TO RELATED APPLICATIONS

This application is a 35 U.S.C. §371 filing of PCT/KR2012/005083 filed Jun. 27, 2012, which claims priority from Korean Patent Application No. 10-2011-0063075 filed Jun. 28, 2011, the disclosures of which are hereby incorporated by reference.

TECHNICAL FIELD

The present invention relates to a time-temperature indicator in the form of a two-dimensional code, whose color or shape varies depending on time and temperature conditions, a method for manufacturing the time-temperature indicator, a quality guarantee system using the time-temperature indicator, and a quality guarantee method using the quality guarantee system.

BACKGROUND

The quality of many products sold to consumers has a range of environmental conditions, and the value of a product depreciates due to spoilage, etc. under improper temperature conditions that are beyond the range.

For example, a food spoils when it is not stored and distributed within a proper temperature range, and when a product that requires refrigerated distribution, such as a prepared medicine, is exposed to an environment outside an allowable temperature range, it cannot perform or deliver its expected function. Moreover, when a food that is susceptible to microbial contamination is exposed to undesirable temperatures, it cannot be eaten due to microbial growth.

Therefore, when a product is made of perishable material, it is important to determine the lifespan of the material and determine whether the product can be currently used.

To this end, an expiration date has been marked on a packing material so far, but it is impossible to accurately determine the state of the product only with the marked expiration date. In particular, the state of a perishable product generally has a great correlation with time and temperature conditions.

Moreover, it is possible to easily change the expiration date, and thus it is insufficient to give enough confidence to a consumer that consumes the corresponding product.

Meanwhile, a Quick Response (QR) code, which was developed by Denso Wave Inc. in 1994, is a matrix-type two-dimensional code in which the same number of small square dots is arranged lengthwise and breadth-wise and includes various versions ranging from 21 to 177 rows/columns (Version 40).

Furthermore, unlike a barcode, the QR code has finder patterns located at three corners of the matrix and thus is readable in any direction of 360 degrees. The largest QR code (Version 40) can record information of up to 23,648 bits. The QR code is printed on a signboard or newspaper to deliver information.

So far, there is no method available to automatically track and identify a product that is exposed to an undesirable environment from the time when the product is manufactured or packed until it reaches its final destination.

Therefore, there is a need to provide a method for detecting any environmental change in temperature and identifying a product with reliability or usefulness that is considered as being potentially dangerous.

SUMMARY

Technical Problem

The present invention has been made to meet the requirements described above, and an object of the present invention is to provide a time-temperature indicator and its manufacturing method, and a quality guarantee system using the time-temperature indicator and a quality guarantee system using the same, which can rapidly and accurately determine whether a product spoils as it is exposed to temperature or time conditions outside an allowed range.

Technical Solution

The present invention provides a time-temperature indicator comprising nanobeads including microorganisms that produce a acidic biological product using nutrients, a base including an adhesive layer, and a cover film having a fixed water activity (Aw) for activation of the microorganisms.

Moreover, the present invention provides a method for manufacturing a time-temperature indicator, the method comprising the steps of: (a) mixing psychrotrophic lactic acid bacteria that produce lactic acid using nutrients and are selected from the group consisting of *Lactobacillus* spp., *Leuconostoc* spp., and *Weissella* spp., an indicator that indicates a change in color by means of the psychrotrophic lactic acid bacteria, an immobilization material that immobilizes the microorganisms and the indicator, and the nutrients; (b) obtaining nanobeads in a gel state by spraying the mixture to a calcium salt solution or strontium salt solution and leaving the resulting mixture; (c) immobilizing the obtained nanobeads, which contain microorganisms that produce a biological product, on a base including an adhesive layer in a single particle layer using air injection; and (d) bringing a cover film, which comprises a aqueous gel containing a polypropylene film, an adhesive, and a saturated salt substance and has a water activity of 0.98 or higher, into contact with the nanobeads.

In addition, the present invention provides a quality guarantee system comprising: the time-temperature indicator; a terminal that includes a camera module for photographing a two-dimensional code, a code recognition unit for decoding an image of the photographed two-dimensional code, and a communication module for transmitting code data of the decoded two-dimensional code; and a central server that receives the code data from the terminal and transmits color information or product information, which corresponds to the code data and is received from a color determination database including the color information about a change in color of the time-temperature indicator or from a product information database including the product information about a product to which the time-temperature indicator is attached, to the terminal.

Additionally, the present invention provides a guarantee method comprising the steps of: (a) generating an image of a two-dimensional code formed on the time-temperature indicator using a camera module included in a terminal; (b)

decoding the generated image of the two-dimensional code and transmitting code data of the decoded two-dimensional code to a central server; (c) extracting color information or product information corresponding to the code data from the central server that includes a color determination database storing the color information about a change in color of the time-temperature indicator and a product information database storing the product information about a product to which the time-temperature indicator is attached; and (d) transmitting the extracted color information or product information to the terminal.

Advantageous Effects

According the embodiments of the present invention, it is possible to rapidly and accurately determine whether a product spoils as it is exposed to temperature or time conditions outside an allowed range.

Moreover, it is possible to give confidence in the distribution process of a product to a consumer that consumes the corresponding product.

BRIEF DESCRIPTION OF THE DRAWINGS

For a further understanding of the nature and objects of the present inventions, reference should be made to the following detailed disclosure, taken in conjunction with the accompanying drawings, in which like parts are given like reference numerals, and wherein.

DETAILED DESCRIPTION OF THE DRAWINGS

Hereinafter, exemplary embodiments of the present invention will be described with reference to the accompanying drawings. In the following description, the same elements will be designated by the same reference numerals although they are shown in different drawings. Moreover, in the following description of the present invention, a detailed description of known functions and configurations incorporated herein will be omitted when it may make the subject matter of the present invention rather unclear. Furthermore, the exemplary embodiments of the present invention will be described below, but the technical idea of the present invention is not limited thereto and may be practiced by those skilled in the art.

The present invention generates a two-dimensional code using a microbial time-temperature indicator (MTTI) whose color varies in a time and temperature dependent manner to allow a user to rapidly identify the quality of a product using the two-dimensional code.

The two-dimensional code may be generated by immobilizing a pH indicator, microorganisms, nutrients, etc. in a nanoscale size and may be used as a tamper-proof label formatted such that a consumer can identify a food that spoils as it is exposed to time or temperature conditions over a limited range with the naked eye or using a predetermined terminal anywhere from the production stage until it reaches the consumer.

Figure 1:
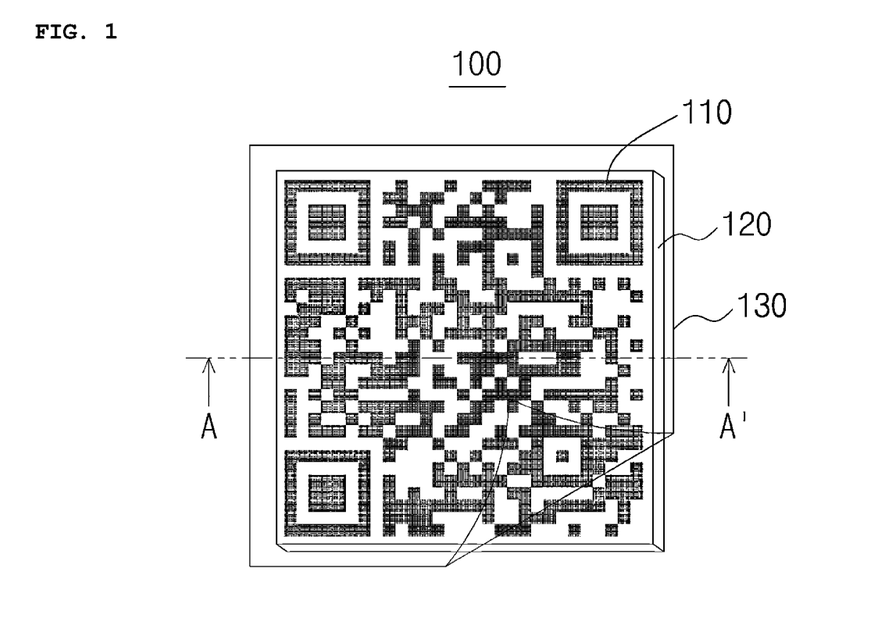
FIG. 1 is a perspective view of a time-temperature indicator in accordance with an exemplary embodiment of the present invention.
Figure 2:
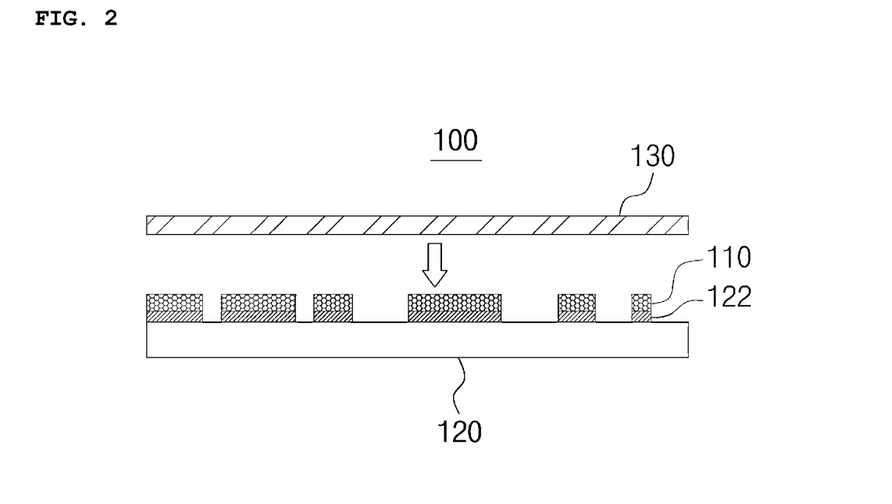
FIG. 2 is a cross-sectional view taken along line A-A' of FIG. 1.

FIG. 1 is a perspective view of a time-temperature indicator in accordance with an exemplary embodiment of the present invention, and FIG. 2 is a cross-sectional view taken along line A-A' of FIG. 1.

Next, the time-temperature indicator 100 in accordance with an exemplary embodiment of the present invention will be described with reference to FIGS. 1 and 2.

The time-temperature indicator 100 in accordance with an exemplary embodiment of the present invention comprises nanobeads 110, a base 120, and a cover film 130.

The nanobeads 110 contain microorganisms that produce lactic acid using nutrients, an indicator that indicates a change in color by means of the produced lactic acid, an immobilization material that immobilizes the microorganisms and the indicator, and the nutrients.

Here, the microorganisms may be psychrotrophic lactic acid bacteria selected from the group consisting of *Lactobacillus* spp., *Leuconostoc* spp., and *Weissella* spp.

The psychrotrophic lactic acid bacteria maintain their inactive state at a temperature lower than 5° C. and are gradually activated in a temperature range of 5-15° C. Therefore, when the time-temperature indicator 100 using the psychrotrophic lactic acid bacteria is applied to a product, such as a medicine or food, which needs to be stored and distributed while maintaining its freshness in a low temperature condition, it is possible to accurately check the storage and distribution state of the product.

As the indicator, a pH indicator such as an acid-base indicator, whose color is changed by the lactic acid produced by the psychrotrophic lactic acid bacteria using the nutrients, may be used, and any type of acid-base indicator may be used as long as it does not affect the microorganisms.

The immobilization material, which immobilizes the microorganisms, the indicator, and the nutrients, may comprise at least one selected from the group consisting of alginic acid, agar, carrageenan, polyacrylamide, and a mixture thereof.

It is preferable that the nanobeads 110 have a diameter of 10-35 nm.

When the cover film 130 having a fixed water activity (Aw) for the activation is brought into contact with the nanobeads 110 in an ultrafine state, water of the cover film 130 is brought into contact with the microorganisms, and thus lactic acid is produced by microbial growth. Therefore, a significant change in color occurs due to a decrease in pH, and thus it is possible to obtain more precise data by the time-temperature indicator 100.

The base 120 includes an adhesive layer 122 on its surface where the nanobeads 110 are to be applied.

Here, the adhesive layer 122 included in the base 120 may be formed by cross-linking a first polymer having a butadiene skeleton part and a second polymer, which is different from the first polymer, in the presence of an organic peroxide.

The base 120 may be formed of metal, nonferrous metal, ceramic, plastic, or paper.

The cover film 130 comprises a aqueous gel containing a polypropylene film, an adhesive, and a saturated salt substance and has a water activity of 0.98 or higher to provide water during the activation of the time-temperature indicator 100.

The nanobeads 110 bonded to the surface of the base 120 by the adhesive layer 122 are applied to the surface of the base 120 in a single particle layer to form the shape of the two-dimensional code or a portion of the two-dimensional code as shown in FIG. 1. That is, the two-dimensional code or a portion of two-dimensional code is formed on the surface of the base 120 using the nanobeads 110 as a kind of ink.

The two-dimensional code made up of the nanobeads 110 can be recognized by a code recognition means. Examples of the two-dimensional code may include QR code, micro QR code, PDF417 code, Data Matrix code, Maxi code, Veri code, Cadablock code, Aztec code, Calula code, BP04 State code, Postnet code, etc.

The two-dimensional code made up of the nanobeads 110 may preferably be a QR code or micro QR code.

Figure 3:
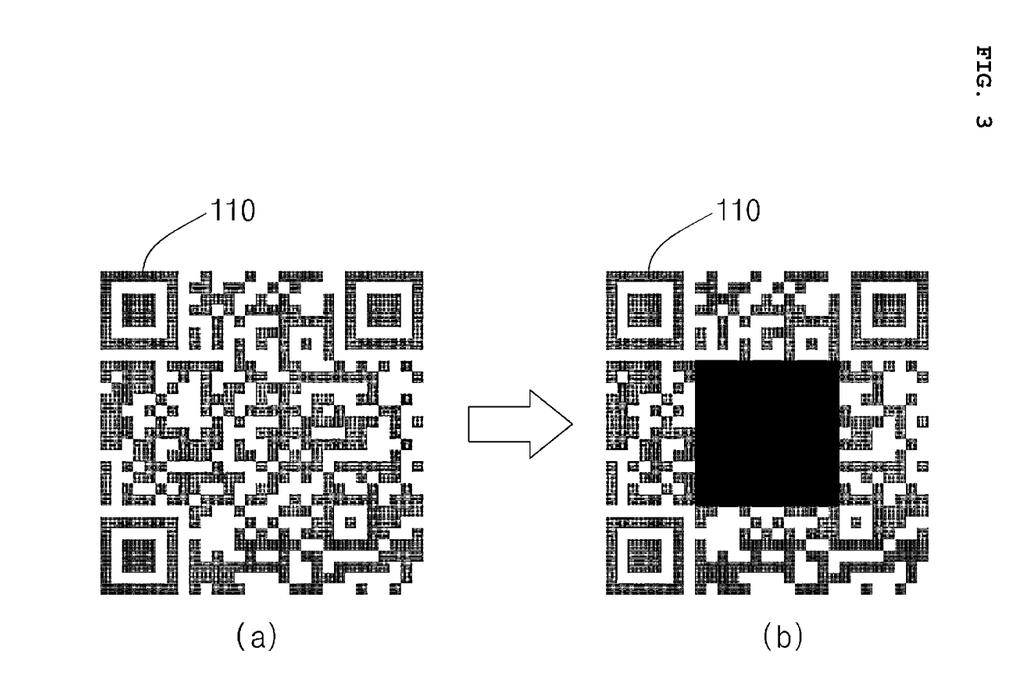
FIG. 3 is a diagram showing an example in which a two-dimensional code made up of nanobeads is deformed.

FIG. 3 is a diagram showing an example in which a two-dimensional code made up of nanobeads is deformed.

When the two-dimensional code made up of the nanobeads 110 is outside predetermined time or temperature conditions under which the microorganisms are in an inactive state, the color or contrast of the nanobeads 110 varies, and thus the shape of the two-dimensional code also varies.

For example, as shown in FIG. 3A, after a portion of the QR code is formed on the base 120 using the nanobeads 110, if the time-temperature indicator 100 is exposed to an environment outside time or temperature conditions, the color or contrast of the nanobeads 110 varies, and thus the QR code of FIG. 3A is deformed to a QR code with a new shape as shown in FIG. 3B.

In other words, the time-temperature indicator 100 in accordance with an exemplary embodiment of the present invention has the form of a QR code label on which a QR code having a variable shape is printed.

The QR codes before and after the deformation have different data values, and thus it is possible to easily identify information related to the state of a product with the lapse of time and information related to the distribution process of the product using the data values.

Figure 4A:
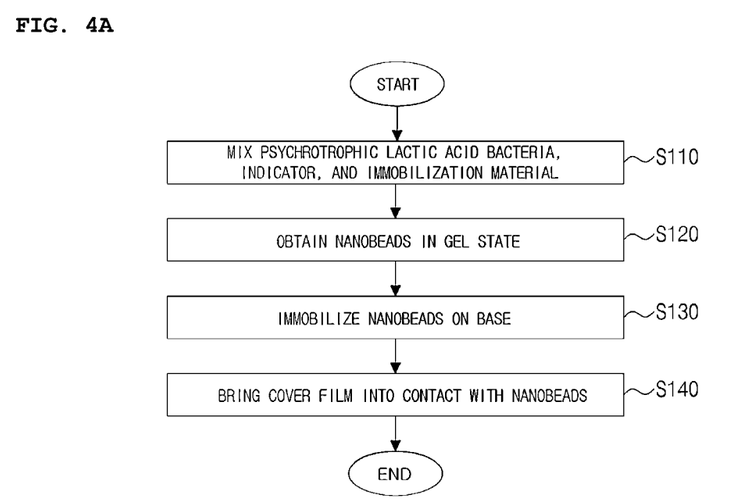
FIGS. 4A to 4C are flowcharts showing a method for manufacturing a time-temperature indicator in accordance with an exemplary embodiment of the present invention.
Figure 4B:
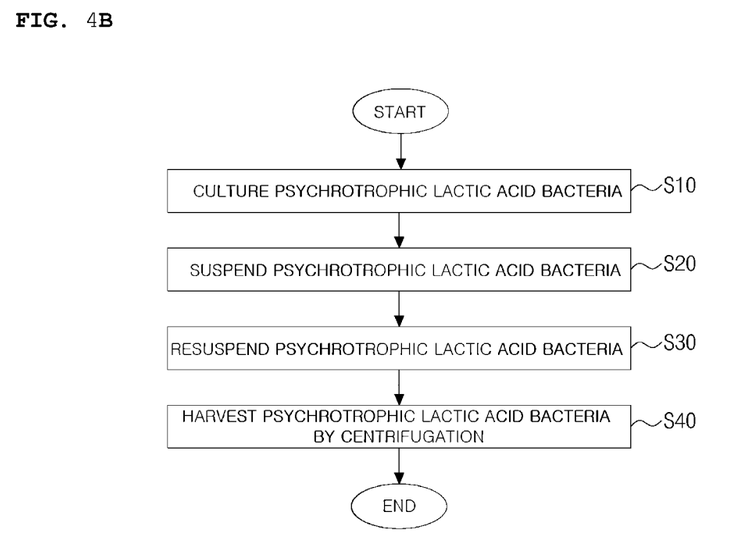
Figure 4C:
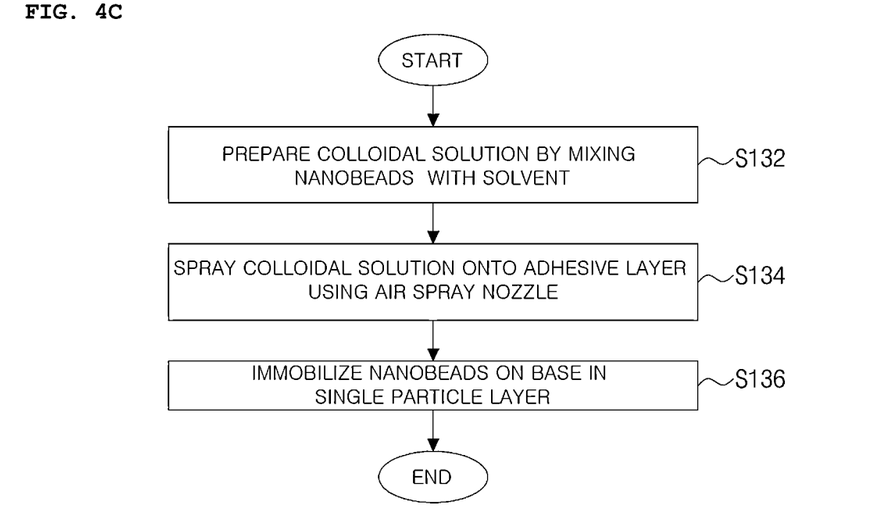
Figure 5:
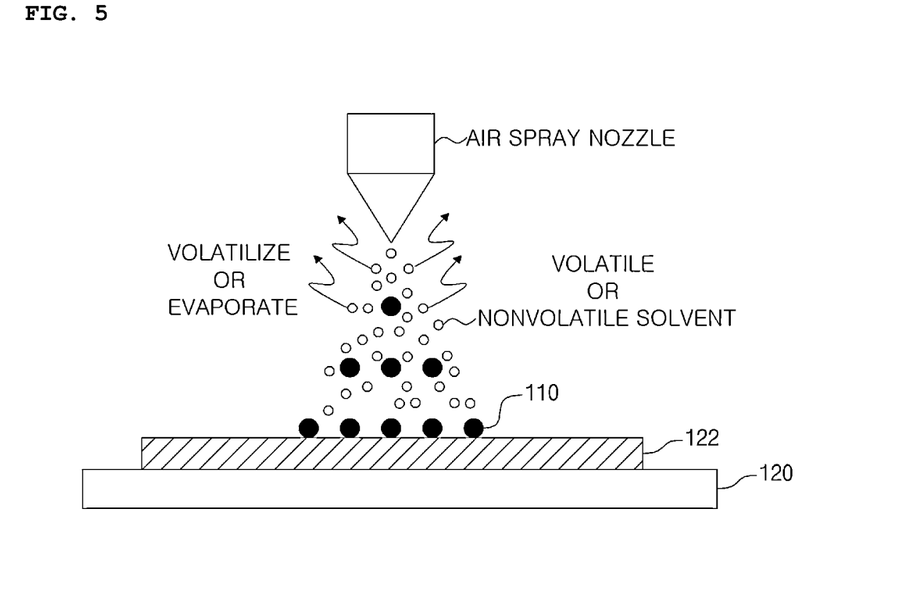
FIG. 5 is a diagram showing a process of immobilizing nanobeads on a base in a single particle layer.

FIGS. 4A to 4C are flowcharts showing a method for manufacturing a time-temperature indicator in accordance with an exemplary embodiment of the present invention, and FIG. 5 is a diagram showing a process of immobilizing nanobeads on a base in a single particle layer.

Next, the method for manufacturing a time-temperature indicator in accordance with an exemplary embodiment of the present invention will be described with reference to FIGS. 4A to 4C and FIG. 5.

To manufacture a time-temperature indicator 100 in accordance with an exemplary embodiment of the present invention, first of all, microorganisms that produce lactic acid using nutrients, such as psychrotrophic lactic acid bacteria selected from the group consisting of *Lactobacillus* spp., *Leuconostoc* spp., and *Weissella* spp., an indicator that indicates a change in color by means of the psychrotrophic lactic acid bacteria, an immobilization material that immobilizes the microorganisms and the indicator, and the nutrients are mixed (S110).

Here, the indicator is a pH indicator, and the immobilization material may be a sodium alginate solution.

Meanwhile, the psychrotrophic lactic acid bacteria may be mixed in step S110 after high-density culture. The high-density culture of psychrotrophic lactic acid bacteria may be performed in a manner shown in FIG. 4B.

More specifically, the psychrotrophic lactic acid bacteria and CaCO3 are immobilized with alginic acid and cultured in MRS broth at 22-27° C. for 45-50 hours (S10), and the psychrotrophic lactic acid bacteria are harvested from the broth by centrifugation and suspended in peptone water (S20).

Here, the MRS broth contains 15-20% CaCO3 beads immobilized with alginic acid, and the smaller size of CaCO3 beads is more suitable for the high-density culture.

After step S20, the psychrotrophic lactic acid bacteria suspended in peptone water is harvested by centrifugation and then resuspended in 2-3% saline solution (S30).

Through steps S20 and S30, the psychrotrophic lactic acid bacteria can be cleanly washed, and polysaccharides produced by the psychrotrophic lactic acid bacteria can be removed.

Lastly, the psychrotrophic lactic acid bacteria suspended in saline solution are harvested by centrifugation (S40).

Since it is possible to culture the psychrotrophic lactic acid bacteria in the above manner, it is easy to obtain microbial cells, and it is possible to reduce the manufacturing cost of the time-temperature indicator 100.

After step S110, the mixture is sprayed to a calcium salt solution or strontium salt solution as an immobilization material and the resulting mixture is left at 0-5° C. for 1-3 hours, thus obtaining nanobeads 110 in a gel state (S120).

The thus obtained nanobeads 110 have no color interference due to colonies representing microbial growth and have a diameter of 10-35 nm. When a cover film 130 having a fixed water activity (Aw) is brought into contact with the nanobeads 110, water is rapidly absorbed into the nanobeads 110 such that the psychrotrophic lactic acid bacteria can sensitively respond to the temperature and thus can effectively produce lactic acid. Therefore, it is possible to easily determine the difference in color change of the time-temperature indicator 100 and obtain more precise data.

After step S120, the obtained nanobeads 110 in a gel state are immobilized on the surface of a base 120 having an adhesive layer 122 (S130).

Specifically, step S130 is performed in the order shown in FIG. 4C. First, a colloidal solution containing the nanobeads 110 is prepared (S132). The colloidal solution is prepared by mixing the nanobeads 110 with a volatile or nonvolatile solvent.

Then, the prepared colloidal solution in a high-pressure gaseous state is sprayed onto the surface of the base 120 having the adhesive layer 122 using an air spray nozzle (S134).

When the volatile solvent in the colloidal solution dispersed on the adhesive layer 122 is volatilized, the nanobeads 110 are bonded to the surface of the adhesive layer 122 to form a single particle layer as shown in FIG. 5 (S136).

Here, when the dispersed colloidal solution is a nonvolatile solvent, the solvent is dried under mild conditions using a typical drying method such as reduced-pressure evaporation, lyophilization, etc. such that the nanobeads 110 are bonded to the surface of the adhesive layer 122.

The nanobeads 110 and the base 120 are strongly bonded by the adhesive layer 122 and thus exhibit significant resistance to being washed or separated.

The nanobeads 110 form the shape of a two-dimensional code recognizable by a code recognition means and, preferably, form the shape of a QR code or micro QR code. Here, it is preferable that the amount of microorganisms forming the two-dimensional code of the time-temperature indicator 100 is 103-107 CFU/g.

Figure 6:
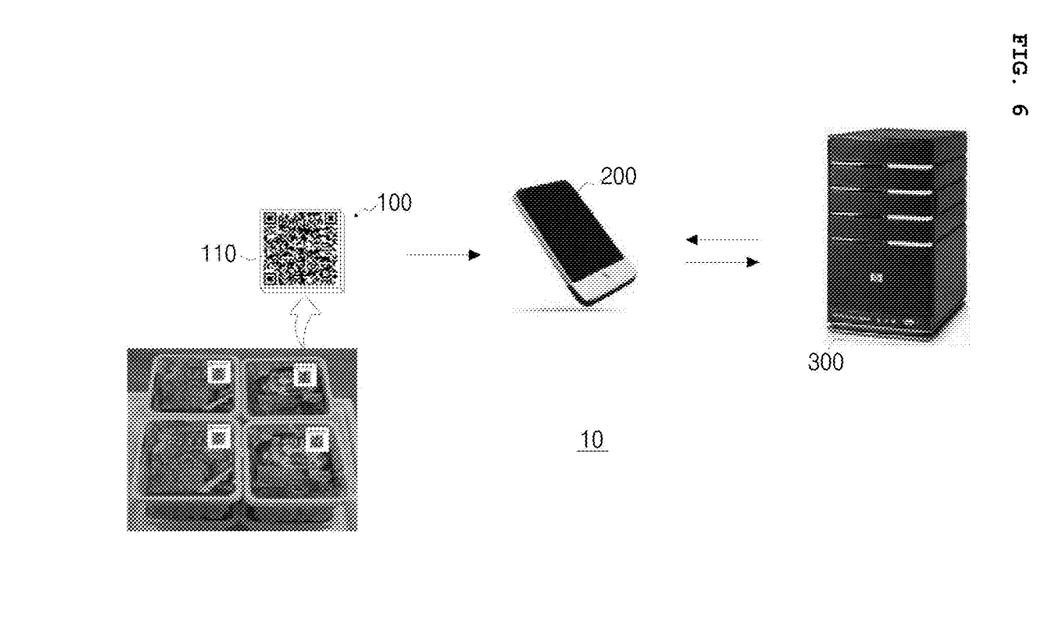
FIG. 6 is a diagram schematically showing a quality guarantee system using a time-temperature indicator in accordance with an exemplary embodiment of the present invention.
Figure 7:
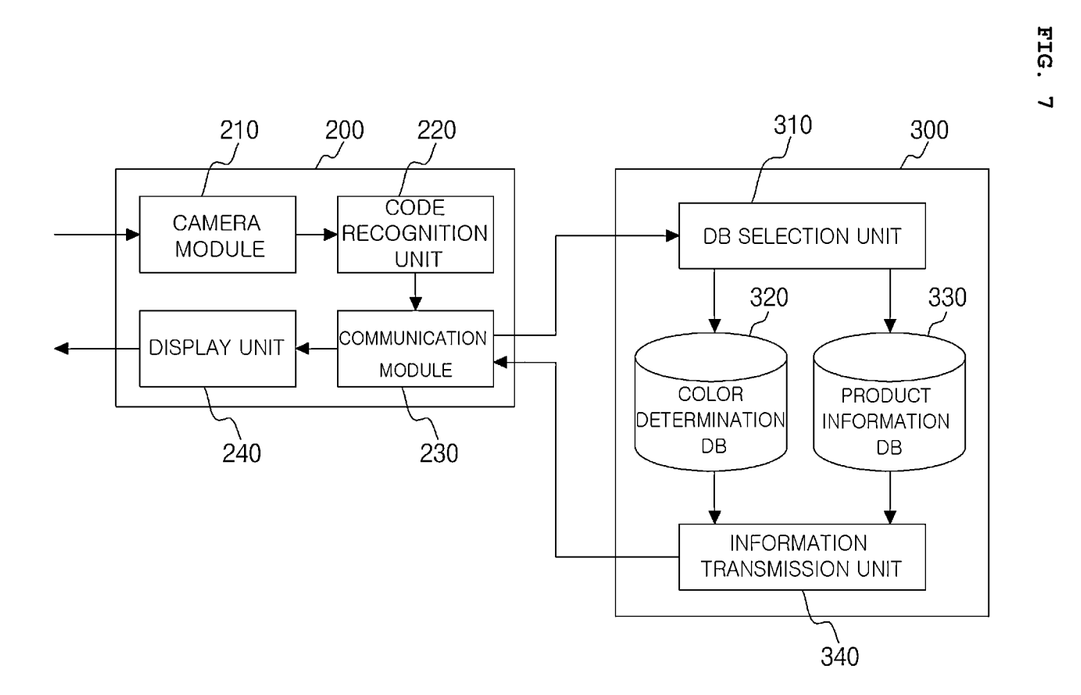
FIG. 7 is a block diagram of a terminal and a central server.

FIG. 6 is a diagram schematically showing a quality guarantee system using a time-temperature indicator in accordance with an exemplary embodiment of the present invention, and FIG. 7 is a block diagram of a terminal and a central server.

Next, the quality guarantee system 10 using a time-temperature indicator in accordance with an exemplary embodiment of the present invention will be described with reference to FIGS. 6 and 7.

The quality guarantee system 10 using a time-temperature indicator in accordance with an exemplary embodiment of the present invention comprises a time-temperature indicator 100, a terminal 200 for recognizing a two-dimensional code, and a central server 300.

Here, the two-dimensional code made up of the nanobeads 110 is printed on the time-temperature indicator 100 as mentioned above.

The terminal 200 is configured to recognize and decode the two-dimensional code formed on the time-temperature indicator 100 and to transmit code data of the decoded two-dimensional code to the central server 300 and may be implemented as a cellular phone, or smart phone, etc.

Specifically, the terminal 200 comprises a camera module 210, a code recognition unit 220, a communication module 230, and a display unit 240.

The camera module 210 serves to photograph a two-dimensional code and generate a digitized image. The camera module 210 may be implemented as a digital imaging device provided with an image sensor such as a charge-coupled device (CCD) sensor or complementary metal-oxide semiconductor (CMOS) sensor.

The code recognition unit 220 decodes the image of the two-dimensional code generated by the camera module 210 and generates code data.

Here, the code data may have a data structure shown the following table 1:

TABLE 1

| A | B | | | C | | | | | | | | | | D | | | | | | | | | |
|---|---|---|---|---|---|---|---|---|---|---|---|---|---|---|---|---|---|---|---|---|---|---|---|
| 0 | 0 | 1 | 0 | 1 | 0 | 0 | 1 | 1 | 0 | 0 | 1 | 1 | 0 | 1 | 0 | 1 | 0 | 0 | 1 | 0 | 1 | 1 | ... |

In Table 1, section A is the identifier field, section B is the DB type field, section C is the serial number field, and section D is the text data field.

The structure of the code data will now be described. The identifier field is to determine whether the two-dimensional code is intended to be decoded by the code recognition unit 220, the DB type field is to select any one of a color determination database 320 and a product information database 330 which are comprised in the central server 300, and the serial number field is to extract color information or product information corresponding to a data value assigned by the selected color determination database 320 or product information database 330.

Moreover, the text data field is to output information in the form of a text, decoded by the code recognition unit 220, to the display unit 240 of the terminal 200.

The code recognition unit 220 determines whether a data value assigned to the identifier field is identical to a pre-stored identification data value and, if the data value assigned to the identifier field is identical to the identification data value, obtains data values assigned to the DB type field and the serial number field.

In detail, the code recognition unit 220 obtains the upper bits of the decoded code data, i.e., the data value of the identifier field, and determines whether the data value is identical to the pre-stored identification data value.

In Table 1, 3 bits are assigned as data bits of the identifier field and, in this case, the code recognition unit 220 can determine the data value of the identifier field by obtaining the upper three bits.

Here, when the identification data and the data value assigned to the identifier field coincide with each other, it is possible to process the DB type field and the serial number field shown in sections B and C in Table 1.

The reason is that when the data value of the identifier field of upper three bits coincides with the identification data value in the example of Table 1, it is possible to confirm that the next ten bits can indicate the DB type field and the serial number field.

Meanwhile, although the code data are expressed as a data structure of 24 bits to facilitate understanding, the QR code (Version 40) can record information of 23,648 bits. Therefore, the rest other than the upper bits corresponding to the identifier field, the DB type field, and the serial number code can be used as the text data field.

The communication module 230 serves to transmit the code data of the decoded two-dimensional code to the central server 300 using a wired or wireless communication method or to receive color information or product information, which will be described later, from the central server 300.

For example, the communication module 230 may be implemented as a CDMA adapter or a Wi-Fi (wireless LAN) adapter according to the IEEE 801.11g or 11n standard and serves to perform data communication through a mobile communication network or communication with a content server through a wireless Internet connection via Wi-Fi. Here, a URL for connecting to the central server 300 may be pre-stored in the code recognition unit 220 of the terminal 200.

The display unit 240 displays text information corresponding to the text data field as mentioned above, color information, or product information on a screen and may be implemented as a typical display means.

The central server 300 comprises a DB selection unit 310, a color determination database 320, a product information database 330, and an information transmission unit 340.

The DB selection unit 310 serves to receive the code data from the communication module 230 and to select a database corresponding to the data value assigned to the DB type field from the color determination database 320 and the product information database 330.

The DB selection unit 310 includes a reception unit (not shown) for receiving the code data.

The color determination database 320 stores color information about a change in color of the time-temperature indicator 100, and the product information database 330 stores product information about a product to which the time-temperature indicator 100 is attached.

The information transmission unit 340 searches for the color information or product information, which corresponds to the data value assigned to the serial number field, from the database selected by the DB selection unit 310 and transmits the information to the terminal 200.

The information transmission unit 340 may include a CDMA adapter or Wi-Fi (wireless LAN) adapter according to the IEEE 801.11g or 11n standard, like the communication module 230.

Figure 8:
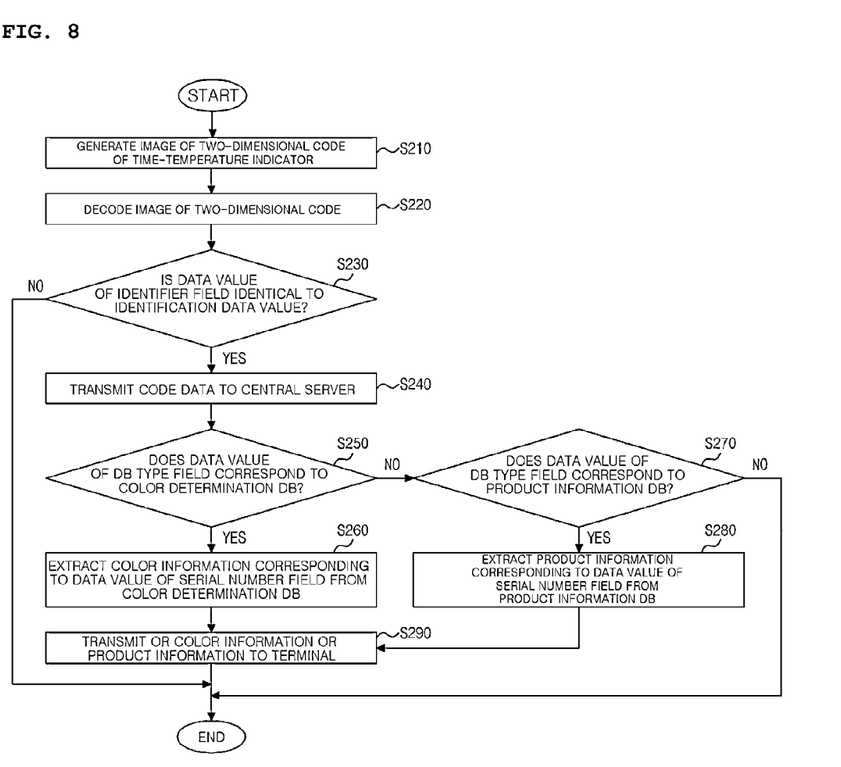
FIG. 8 is a flowchart showing a quality guarantee method using a quality guarantee system in accordance with an exemplary embodiment of the present invention.

FIG. 8 is a flowchart showing a quality guarantee method using a quality guarantee system in accordance with an exemplary embodiment of the present invention.

Next, the quality guarantee method using the quality guarantee system 10 in accordance with an exemplary embodiment of the present invention will be described with reference to FIG. 8.

First, the camera module 210 generates an image of a two-dimensional code of the time-temperature indicator 100 attached to a product or a package of the product (S210).

The code recognition unit 220 decodes the generated image of the two-dimensional code (S220) and determines whether a data value of an identifier field included in code data of the decoded two-dimensional code is identical to a pre-stored identification data value (S230).

Here, if the data value of the identifier field is identical to the identification data vale, the communication module 230 transmits a data value of a DB type field and a data vale of a serial number field, which are included in the code data, to a DB selection unit 310 of a central server 300 (S240).

The DB selection unit 310 selects a database having a data value corresponding to the received data value of the DB type field from the color determination database 320 and the product information database 330 to which a predetermined data value is assigned in advance, respectively.

For example, the DB selection unit 310 determines whether the data value of the DB type field corresponds to the data value assigned to the color determination database 320 (S250), and if it is determined that both data values are identical to each other, the information transmission unit 340 extracts color information corresponding to the data value of the serial number field from the color determination database 320 (S260) and transmits the extracted color information to the terminal 200 (S290).

The terminal 200 outputs the color information received through the communication module 230 on a screen through the display unit 240.

If the data value of the DB type field does not correspond to the data value of the color determination database 320 in step S250, the DB selection unit 310 determines whether the data value of the DB type field corresponds to the data value assigned to the product information database 330 (S270), and if it is determined that both data values are identical to each other, the information transmission unit 340 extracts product information corresponding to the data value of the serial number field from the product information database 330 (S280) and transmits the extracted product information to the terminal 200 (S290).

Although not shown, the central server 300 may include a database storing both the color information and the product information to which data values are assigned so as to search for information corresponding to the data value assigned to a specific section and transmit the information to the terminal 200.

Meanwhile, the data value of the DB type field of the decoded two-dimensional code in a normal state as shown in FIG. 3A may correspond to the product information database 330 such that a consumer can identify information of the corresponding product with the freshness.

The data value of the DB type field of the decoded two-dimensional code with a change in shape depending on time or temperature conditions as shown in FIG. 3B may correspond to the color determination database 320 to provide the consumer with a warning message about the possibility of spoilage of the product or information for determining whether to purchase the product.

Figure 9:
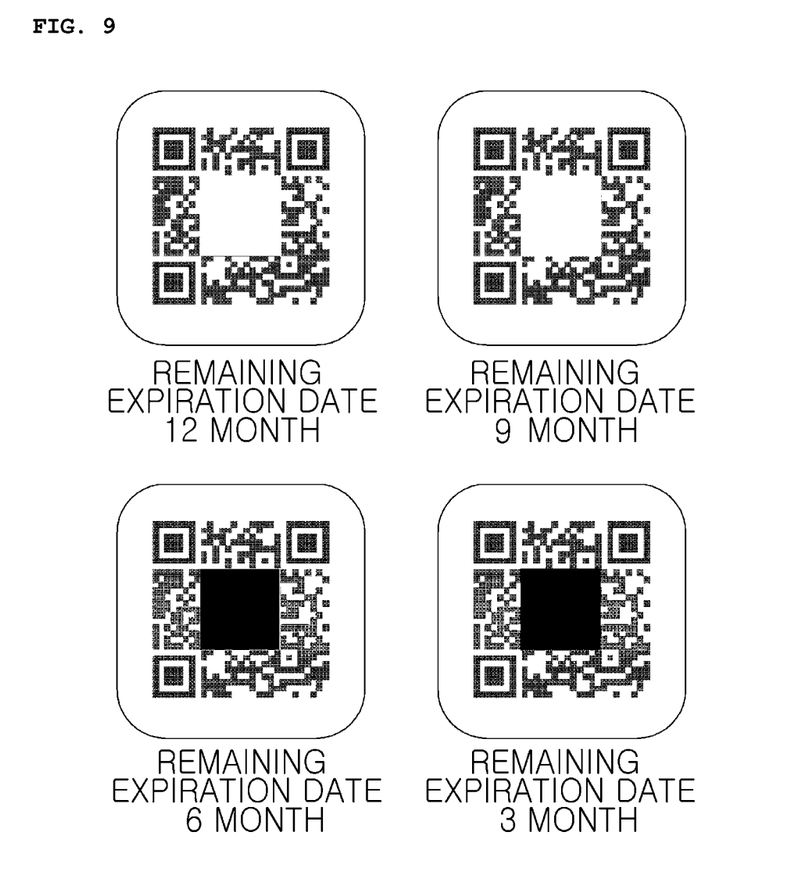
FIG. 9 is a diagram showing examples of screens on which color information is displayed.

FIG. 9 is a diagram showing examples of screens on which color information is displayed.

The color information may be configured as a standard table allowing the user to determine the change in color of the time-temperature indicator 100.

For example, as shown in FIG. 9, the color information may be implemented as an image indicating the discoloration process of the time-temperature indicator 100 and the remaining expiration date, Preferably, the image of the color information is provided as the same image taken by a terminal of the same type as the terminal 200 photographing the two-dimensional code to prevent the color from changing due to a difference in the type of the terminal.

The product information may comprise a web page URL including the description of a product to which the time-temperature indicator 100 is attached, a product type code, etc.

The time-temperature indicator in accordance with the embodiment of the present invention has advantages that can effectively indicate a clear, continuous, and irreversible change in temperature and has no toxicity. Moreover, it is economical due to its low manufacturing cost that does not affect the price of a product.

The present invention allows a consumer to monitor time-temperature history information using a two-dimensional code such as a Quick Response (QR) code and is applicable to a product whose freshness is an important quality index or a product that requires cold-chain distribution and that is prohibited to be distributed or required to be removed when it is exposed to undesirable temperature conditions.

Moreover, the present invention can help a manufacturer, a processor, a distributor, a hygiene officer, and a consumer to pay attention to a product that has high possibility of secondary microbial contamination and reduced quality due to damage during cold-chain distribution and can provide useful history data related to the event.

Although the above description is only an illustrative description of the technical idea of the present invention, those having ordinary knowledge in the technical field of the present invention will appreciate that various modifications, additions and substitutions are possible, without departing from the scope and spirit of the invention as disclosed in the appended claims. Therefore, the embodiments disclosed in the present invention are intended to illustrate the scope of the technical idea of the present invention, and the scope of the technical idea of the present invention is not limited by the embodiments. The protection scope of the present invention should be construed based on the accompanying claims, and all of the technical ideas included within the scope equivalent to the claims should be construed as being included within the right scope of the present invention.

The invention claimed is:

1. A time-temperature indicator comprising:
   nanobeads comprising microorganisms that produce lactic acid using nutrients, an indicator that indicates a change in color by means of the produced lactic acid, an immobilization material that immobilizes the microorganisms and the indicator, and the nutrients, wherein the nanobeads contain the microorganisms;

a base comprising an adhesive layer, wherein the adhesive layer is formed by cross-linking a first polymer having a butadiene skeleton part and a second polymer in the presence of an organic peroxide; and a cover film having a fixed water activity (Aw) and brought into contact with the nanobeads to activate the microorganisms.

2. The time-temperature indicator of claim 1, wherein the nanobeads are bonded to the adhesive layer of the base to form a two-dimensional code, and the color or contrast of the nanobeads varies depending on a change in time or temperature to deform the shape of the two-dimensional code.

3. The time-temperature indicator of claim 1, wherein the microorganisms are psychrotrophic lactic acid bacteria selected from the group consisting of *Lactobacillus* spp., *Leuconostoc* spp., and Weissella spp.

4. The time-temperature indicator of claim 1, wherein the immobilization material comprises at least one selected from the group consisting of alginic acid, agar, carrageenan, and polyacrylamide.

5. The time-temperature indicator of claim 1, wherein the second polymer is different from the first polymer.

6. The time-temperature indicator of claim 1, wherein the nanobeads have a diameter of 10-35 nm.

7. A method for manufacturing the time-temperature indicator of claim 1, the method comprising the steps of:
(a) mixing psychrotrophic lactic acid bacteria that produce lactic acid using nutrients and are selected from the group consisting of *Lactobacillus* spp., *Leuconostoc* spp., and Weissella spp., an indicator that indicates a change in color by means of the psychrotrophic lactic acid bacteria, an immobilization material that immobilizes the microorganisms and the indicator, and the nutrients;

(b) obtaining nanobeads in a gel state by spraying the mixture to a calcium salt solution or strontium salt solution and leaving the resulting mixture;
(c) immobilizing the obtained nanobeads on a base comprising an adhesive layer; and
(d) bringing a cover film, which comprises a aqueous gel containing a polypropylene film, an adhesive, and a saturated salt substance and has a water activity of 0.98 or higher, into contact with the nanobeads.

8. The method of claim 7, wherein in the immobilization of the nanobeads on the base in step (c), the nanobeads are immobilized on the adhesive layer of the base so as to form the shape of a two-dimensional code recognizable by a code recognition means.

9. The method of claim 7, wherein step (c) comprises the steps of:
(c1) preparing a colloidal solution by mixing the nanobeads in a gel state with a volatile or nonvolatile solvent;
(c2) spraying the prepared colloidal solution onto the base comprising the adhesive layer using an air spray nozzle; and
(c3) immobilizing the nanobeads on the adhesive layer in a single particle layer by volatilizing or evaporating the solvent in the sprayed colloidal solution.

10. The method of claim 7, further comprising, before step (a), the steps of:
immobilizing the psychrotrophic lactic acid bacteria and CaCO3 with alginic acid and culturing the resulting psychrotrophic lactic acid bacteria in MRS broth;
harvesting the psychrotrophic lactic acid bacteria from the broth by centrifugation and suspending the harvested psychrotrophic lactic acid bacteria in peptone water;
harvesting the psychrotrophic lactic acid bacteria suspended in the peptone water by centrifugation and resuspending the harvested psychrotrophic lactic acid bacteria in 2-3% saline solution; and
harvesting the psychrotrophic lactic acid bacteria resuspended in the saline solution by centrifugation.

* * * * *